US00H002256H

(19) United States
(12) Statutory Invention Registration
Rayms-Keller

(10) Reg. No.: US H2256 H
(43) Published: Jun. 7, 2011

(54) 3-HYDROXY-3-METHYLHEXANOIC ACID AND 3-METHYL-2-HEXANOIC ACID DETECTION AS IDENTIFIERS TO MONITOR HUMAN PRESENCE

(75) Inventor: Alfredo Rayms-Keller, Fredericksburg, VA (US)

(73) Assignee: United States of America as represented by the Secretary of the Navy, Washington, DC (US)

(21) Appl. No.: 11/345,675

(22) Filed: Jan. 30, 2006

(51) Int. Cl.
*G01N 33/497* (2006.01)

(52) U.S. Cl. ..... 422/83; 73/23.34

(58) Field of Classification Search ..... 422/83, 422/86; 436/181; 73/23.34–23.35
See application file for complete search history.

(56) References Cited

U.S. PATENT DOCUMENTS

| | | | | |
|---|---|---|---|---|
| 4,022,054 | A | 5/1977 | Biederman | 73/23 |
| 5,141,921 | A | 8/1992 | Sawano et al. | 512/26 |
| 5,512,274 | A | 4/1996 | Phinney | 424/65 |
| 5,777,207 | A | 7/1998 | Yun et al. | 73/31.05 |
| 5,918,257 | A | 6/1999 | Mifsud et al. | 73/23.34 |
| 5,928,609 | A | 7/1999 | Gibson et al. | 422/90 |
| 6,319,724 | B1 * | 11/2001 | Lewis et al. | 436/149 |
| 6,374,662 | B1 * | 4/2002 | Oda et al. | 73/23.34 |
| 6,495,097 | B1 | 12/2002 | Streit et al. | 422/5 |
| 6,824,513 | B2 | 11/2004 | Jansen | 600/300 |
| 2002/0149466 | A1 * | 10/2002 | Sunshine et al. | 338/34 |
| 2003/0194350 | A1 * | 10/2003 | Stamatelos et al. | 422/83 |
| 2004/0106211 | A1 * | 6/2004 | Kauer et al. | 436/169 |
| 2004/0185574 | A1 * | 9/2004 | McGee et al. | 436/174 |

FOREIGN PATENT DOCUMENTS

WO WO 2004/078154 9/2004

OTHER PUBLICATIONS

James et al. Fatty acid metabolism by cutaneous bacteria and its role in axillary malodor. World Hournal of Microbiology & Biotechnology. vol. 20, pp. 787–793. (2004).*

Hradil et al. Heterogenous membranes based on polymeric adsorbents for separation of small molecules. Reactive and Functional Polymers. vol. 61. pp. 303–313. (2004).*

Das et al. Synthesis and characterization of polyacrylamide–polyaniline conductive blends. Journal of Applied Polymer Science. vol. 69. pp. 841–844. (1998).*

Natsch et al., "A specific bacterial aminoacylase cleaves odorant precursors secreted in the human axilla", *J. Biol. Chem*, 278 (8), pp. 5718–5727, Dec. 4, 2002.

(Continued)

*Primary Examiner*—Dan Pihulic
(74) *Attorney, Agent, or Firm*—Gerhard W. Thielman

(57) ABSTRACT

Various embodiments are described relating to devices and methods for detecting local human presence by olfactory reception of volatile organic compound (VOC) molecules dispersed in air. Such devices include a chamber inlet, a trap, a sensor and a communicator. The inlet receives the air that contains the VOC molecules, a trap for capturing the VOC molecules in the air. The sensor detects at least a threshold quantity of at least one of 3-hydroxy-3-methylhexanoic (3H3MH) acid and 3-methyl-2-hexanoic (3M2H) acid among the VOC molecules. The communicator provides notification of the threshold quantity. The methods include operations to receive the air, capture the molecules in the air, detect the 3H3MH and 3M2H acids, and signal notification of that detection.

22 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OTHER PUBLICATIONS

Hasegawa et al., "Identification of New Odoriferous Compounds in Human Axillary Sweat", *Chemistry & Biodiersity*, 1 (12), pp. 2042–2050, Dec. 22, 2004.

Sommerville et al. Analysis of human sweat volatiles: An example of pattern recognition in the analysis and interpretation of gas chromatograms. Pesticide Science. vol. 41. pp. 365–368. (1994).*

Zeng et al. A human axillary odorant is carried by apolipoprotein D. Proceedings of the National Academy of Sciences of the United States of America. vol. 93. pp. 6626–6630. (Jun. 1996).*

* cited by examiner

3-HYDROXY-3-METHYLHEXANOIC ACID AND 3-METHYL-2-HEXANOIC ACID DETECTION AS IDENTIFIERS TO MONITOR HUMAN PRESENCE

STATEMENT OF GOVERNMENT INTEREST

The invention described herein may be manufactured and used by or for the Government of the United States of America for governmental purposes without the payment of any royalties thereon or therefor.

FIELD OF THE INVENTION

This invention relates to chemical detection of human presence.

BACKGROUND

Government and private officials often have responsibility for controlled areas subject to restrictive access to authorized persons. Such officials may employ various techniques to detect human presence. These tools generally depend on human activity to present a detectable signal.

Human activity may trigger a sensor based on various stimuli. For example, skeletal-muscular physical motion may form pressure gradients in the local environment, either the surrounding air or through the ground. For sufficiently intense pressure gradients, such motion may register motion or audio signals. Complimentarily, metabolic activity may yield a thermal contrast between the temperatures of a human body and the ambient surroundings.

SUMMARY

Various embodiments are described relating to devices and methods for detecting local human presence by the reception and detection of human-specific volatile organic compound (VOC) molecules dispersed in air. According to an example embodiment, such devices include a chamber inlet, a trap, a sensor and a communicator. The inlet receives the air that contains the human-specific VOC molecules, a trap for capturing the VOC molecules in the air.

The sensor detects at least a threshold quantity of at least one of 3-hydroxy-3-methylhexanoic (3H3MH) acid and 3-methyl-2-hexanoic (3M2H) acid among the VOC molecules. The communicator provides notification of the threshold quantity. The methods include operations to receive the air, capture the molecules in the air, detect the 3H3MH and 3M2H acids, and signal notification of that detection.

According to an example embodiment, the trap includes a sieve for capturing the VOC molecules from the air and a heater for releasing the captured VOC molecules from the sieve. In addition, the sensor comprises a chemical analyzer such as, for example, an ion-mobility spectroscope, a gas chromatograph, a gas chromatograph plus a mass spectroscope, and a flame ionization spectroscope. The corresponding exemplary method employs chemical detection of the 3H3MH and 3M2H acids.

According to another example embodiment, the trap comprises a filter that includes polyacrylamide fibers for capturing the VOC molecules from the air. In addition, the sensor comprises an electrode for responding to a physical property change in the polyacrylamide fibers. This physical property change, such as electrical characteristics, is caused by at least one of the 3H3MH and 3M2H acids in the captured VOC molecules. The corresponding exemplary method employs detection of characteristic changes in the filter's electrical properties.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

Motion and thermal detectors require either physical or metabolic activity that cannot distinguish between human presence and non-human stimuli on a consistent or systematical basis. Consequently, sensor indication of movement or thermal contrast may result in false alarms that unproductively expend resources that operatives prefer to conserve. Thus, various exemplary embodiments describe techniques for exploiting human characteristics that exhibit unique and detectable manifestations.

Human skin, especially in axillary (i.e., armpit) regions, produces perspiration secretions whose molecules can be truncated by bacteria to produce hexanoic acids that represent volatile organic compound (VOC) molecules. These VOC molecules produce a recognizable odor and represent a uniquely human chemical signature, at least in detectable quantities. The odor produced by the VOC molecules can be sensed by olfactory receptors. The VOC molecules, as represented by hexanoic acids, include 3-hydroxy-3-methylhexanoic (3H3MH) acid and 3-methyl-2-hexanoic (3M2H) acid. After being captured, these VOC molecules can be heated to increase volatility for spectroscopic detection.

Figure 1:
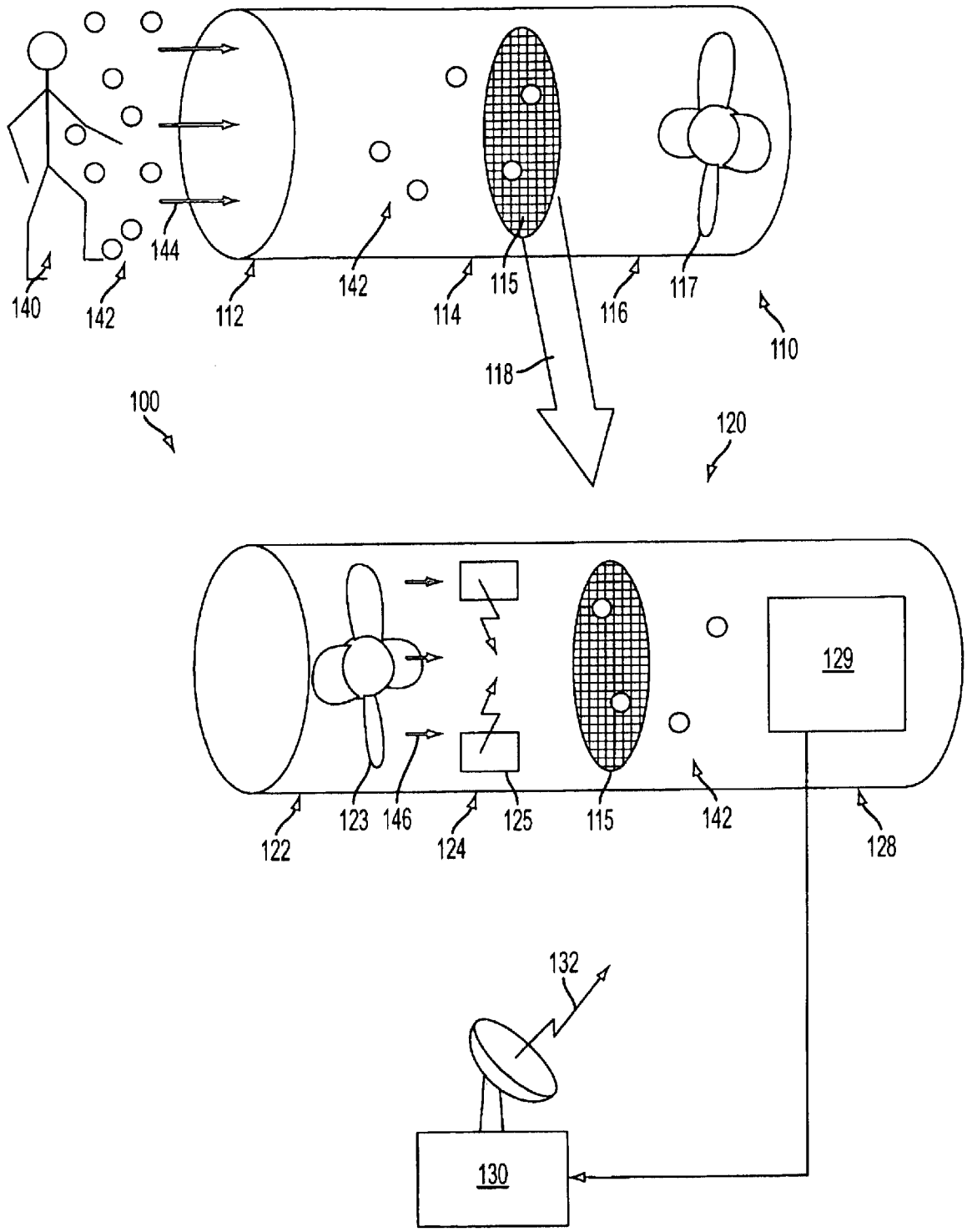
FIG. 1 is a diagram illustrating an olfactory detection system according to a chemical example embodiment.

FIG. 1 is a diagram illustrating a VOC detection system 100 according to an example embodiment. The system 100 includes a pair of hollow chambers, represented by cylindrical tubes. The first chamber 110 is divided into an inlet portion 112 and a first filter portion 114 and a first convection portion 116. The second chamber 120 is divided into a second convection portion 122, a heater portion 124, a second filter portion 126, and an analysis portion 128.

The system 100 further includes a communicator 130. Upon detection of threshold-triggering quantities of 3H3MH and/or 3M2H acids, the communicator or signaler 130 transmits a wireless signal 132 to a remote receiver (not shown) for intrusion and/or threat assessment.

A person 140 within detection vicinity of the system 100 releases VOC molecules 142 into the ambient air 144, A first fan 117 within the first convection portion 116 drives the air 144 into the chamber 110. The molecules 142 in the air 144 enter the inlet portion 112 and pass into a sieve 115 disposed within the first filter portion 114 at a first position. The sieve 115 serves to capture or trap the molecules 142 by filtering the air 144 passing therethrough.

In various exemplary embodiments, the sieve 115 is a polymeric filter that chemically binds to the molecules 142, thereby capturing them in the sieve 115. A transfer mechanism 118 (shown symbolically) may remove the sieve 115 from its first position in the first filter portion 114 to a second position in the second filter portion 126. Alternatively, the sieve 115 may be transferred manually from its first to second filter positions.

The second convection portion 122 includes a second fan 123 with which to blow air 146 over the sieve 115 disposed at the second position. A heater 125 in the heater portion 124, in cooperation with the second fan 123, volatilizes and releases the trapped molecules 142 on the sieve 115 at the second position. The air 146 carries these molecules 142 by convection to the analysis portion 128. The second fan 123 and the heater 125 may be disposed preferably upstream of the filter's second position.

The analysis portion 128 includes a chemical analyzer 129 to evaluate the molecules 142 for the presence of 3H3MH and/or 3M2H acids. Threshold detection determines human presence in the vicinity of the system 100. In various exemplary embodiments, the chemical analyzer 129 may be any of an ion-mobility spectroscope, a gas chromatograph, a gas chromatograph plus a mass spectroscope, or a flame ionization spectroscope. All of these analyzers are available as commercial off-the-shelf (COTS) devices.

Figure 2:
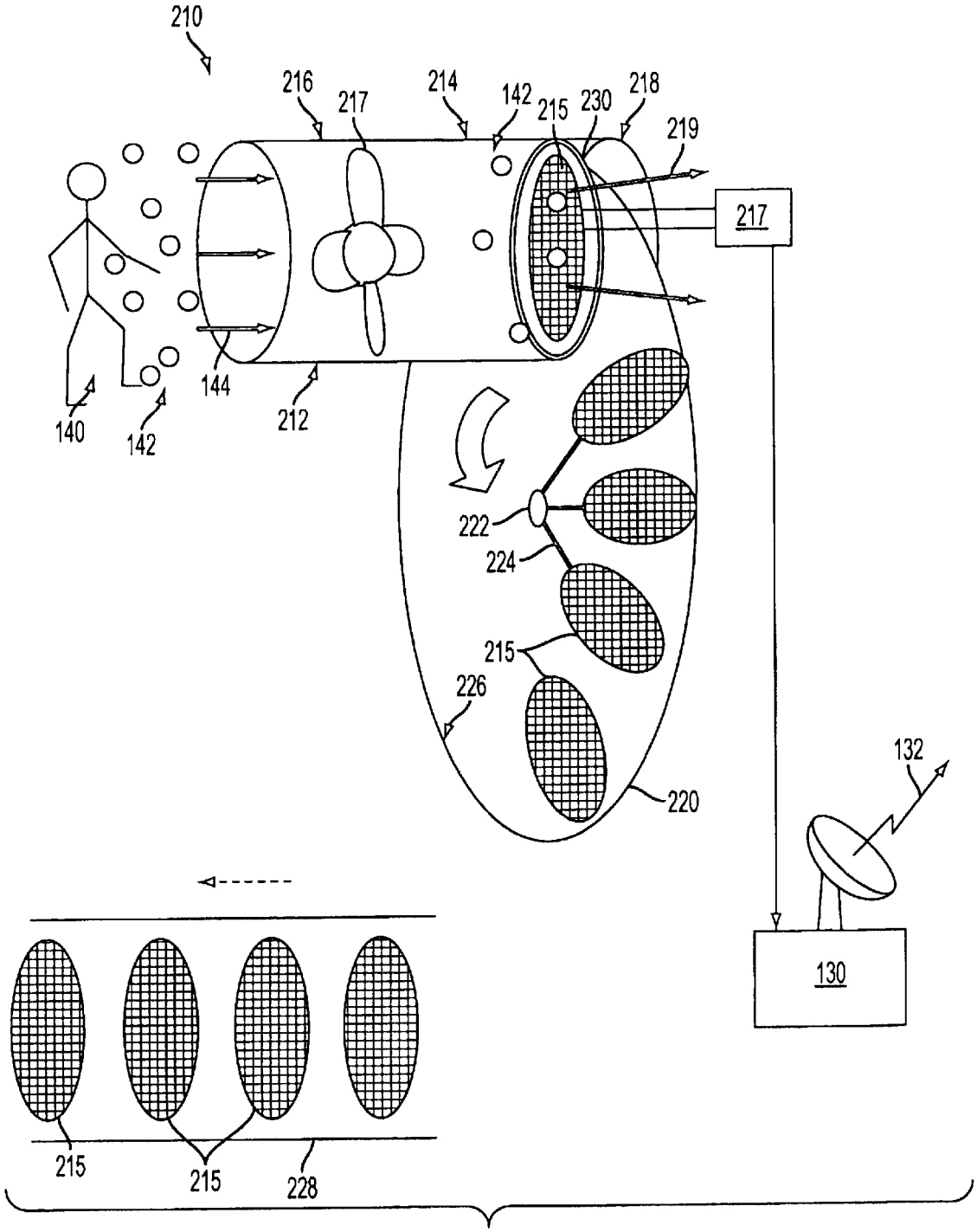
FIG. 2 is a diagram illustrating an olfactory detection system according to an electrical example embodiment.

FIG. 2 is a diagram illustrating a VOC detection system 200 according to an example embodiment. The system 200 includes a hollow chamber 210, represented by a cylindrical tube, divided into an inlet portion 212, a filter portion 214, a convection portion 216 and an outlet portion 218.

A person 140 within the detector's vicinity releases VOC molecules 142 into the ambient air 144. A fan 217 within the convection portion 216 drives the air 144 with molecules 142 towards the chamber 210. The molecules 142 in the air 144 enter the inlet portion 212 and pass through a filter 215 disposed within the filter portion 214.

The filter 215 may include an electrode circuit 217 to sense changes in filter capacitance, conductance and/or light emission. Such physical characteristics are affected for detection by the electrode circuit 217 only when the filter 215 is saturated with 3H3MH and/or 3M2H acids, whereupon the communicator 130 transmits the wireless signal 132 to a remote receiver (not shown) for intrusion and/or threat assessment. The wireless signal 132 represents a radio signal within the electromagnetic spectrum, such as, but not limited to, radio, microwave and infrared frequencies.

In various exemplary embodiments, the filter 215 may include "memory" polymers, such as polyacrylamide. Such memory polymers can be produced via electrospinning techniques. By judiciously incorporating selected chemical additives or "dopants" to the polymer liquid prior to being electrospun, the filter 215 can respond to the binding of 3H3MH and/or 3M2H acids by changes in electrical conductance and/or electrical capacitance.

Dopants for enabling such property change detection by the electrode 217 include electrically conductive metal nanoparticles (particles whose diameter is less than 100 nanometers), such as gold, silver or copper, and/or electroconductive polymers such as polyanilline. Alternatively, in response to binding with the molecules 142 the filter 215 can emit visible light 219 in response to the VOC binding. Dopants for enabling such light emission by the filter 215 include any semi-conducting material such as doped silicon. The light 219 may provide a visual indication of threshold quantities of the molecules 142 for further investigation. The light 219 may be transmitted to an eye-piece or through fiber optics to a remote monitoring station, or be used to trigger a radiofrequency signal by wireless transmission.

In various exemplary embodiments, the filter 215 may be exchanged with another filter, after the initially installed filter becomes saturated or to select an alternate particle size for transmission. The filter 215 may be connected to a tray or carrousel 220 having a series of filters 215. The tray 220 may rotate about a carrousel center 222, as shown, to exchange filters 215 mounted on spokes 224 and/or connected along a rim 226. Alternatively, the tray 220 may translate as a conveyor belt 228 to exchange filters 215. The filter 215 may be inserted through a slot 230 within the filter portion 214.

Figure 3:
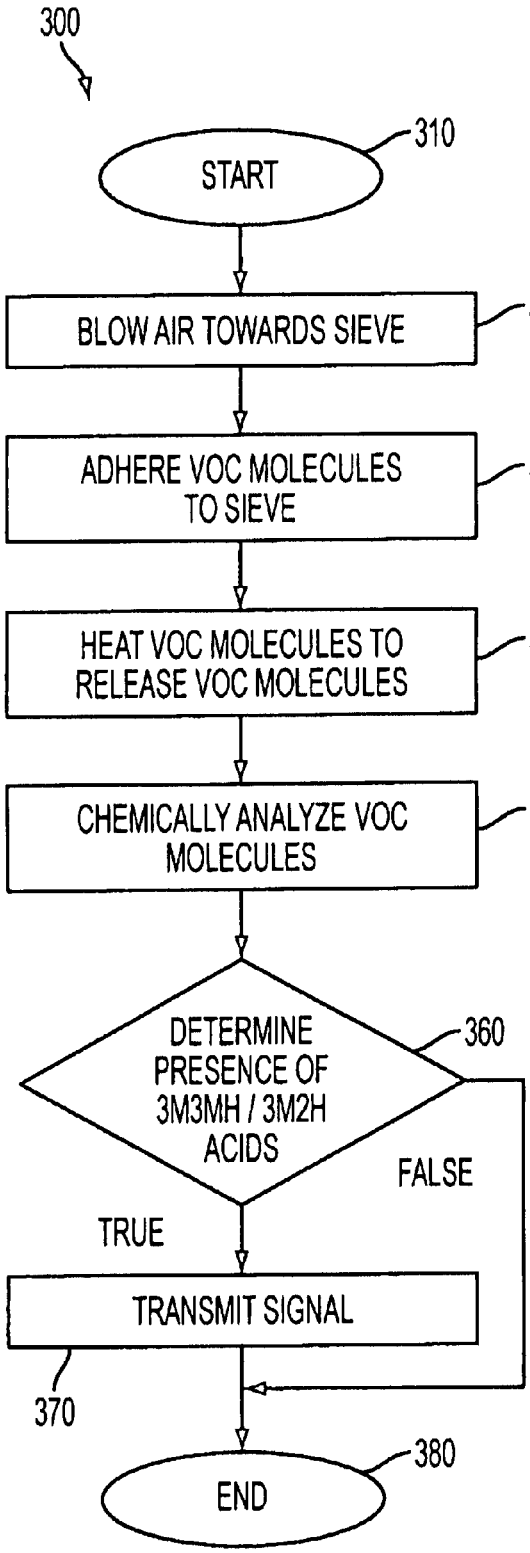
FIG. 3 is a flow diagram illustrating a logical sequence of operations for olfactory detection of human presence according to an example embodiment.

FIG. 3 is a flow diagram illustrating an exemplarily process 300 of logical operations for olfactory detection of the VOC molecules 142 to indicate presence of the person 140. The process begins with at step 310 and proceeds to blowing the air 144 towards a sieve at step 320. The VOC molecules 142 in the air 144 adhere to the sieve 115 at step 330. The heater 121 applied to the sieve 115 releases the molecules 142 at step 340.

The chemical analyzer 129 receives and analyzes the molecules 142 at step 350 to determine at step 360 whether threshold quantities of 3H3MH and/or 3M2H acids are present. Upon such chemical detection, the communicator 130 transmits the signal 132 at step 370 to indicate presence of the person 140. Otherwise, or at the conclusion of signal transmission, the process terminates at step 380.

Figure 4:
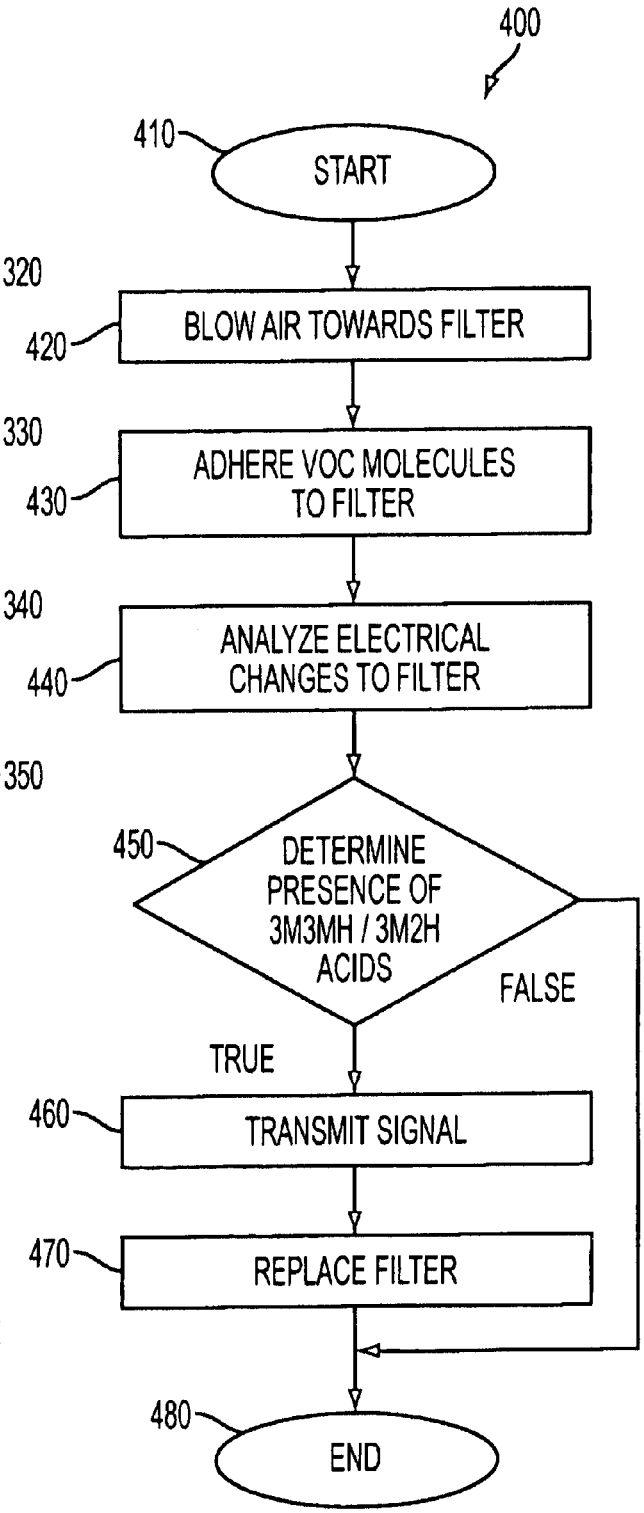
FIG. 4 is a flow diagram illustrating a logical sequence of operations for olfactory detection of human presence according to an example embodiment.

FIG. 4 is a flow diagram illustrating another exemplary process 400 of logical operations for olfactory detection of the VOC molecules 142 to indicate presence of the person 140. The process begins with at step 410 and proceeds to blowing the air 144 towards a filter 215 at step 420. The VOC molecules 142 in the air 144 adhere to the filter 215 at step 430. The electrode circuit 217 connected to the filter 215 evaluates characteristic changes to electrical properties of the filter 215 at step 440 caused by saturation of the VOC molecules 142 to determine at step 450 whether threshold quantities of 3H3MH and/or 3M2H acids are present.

Upon such electrical detection, the communicator 130 transmits the signal 132 at step 460 to indicate presence of the person 140. After reaching VOC molecular saturation, the filter 215 can changed at step 470. In the absence of such detection at step 450, or at the conclusion of signal transmission, the process terminates at step 480.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A device for detecting local human presence by reception and detection of human-specific volatile organic compound (VOC) molecules dispersed in air, the device comprising:

a chamber inlet for receiving the air that contains the VOC molecules;

a trap for capturing the VOC molecules in the air;

a sensor for detecting at least a threshold quantity of 3-hydroxy-3-methylhexanoic (3H3MH) acid among the VOC molecules; and a communicator for providing notification of the threshold quantity.

2. The device of claim 1, wherein the chamber inlet includes a fan for drawing the air that contains the VOC molecules into the trap.

3. The device of claim 1, wherein the trap comprises:

a sieve for capturing the VOC molecules from the air; and a heater for releasing the captured VOC molecules from the sieve.

4. The device of claim 3, wherein the trap further comprises a fan for drawing the released VOC molecules to the sensor.

5. The device of claim 3, wherein the sieve is a polymeric filter that chemically binds to the VOC molecules.

6. The device of claim 4, wherein the sieve captures the VOC molecules at a first position downstream of the chamber inlet and releases the VOC molecules from second position upstream of the sensor.

7. The device of claim 6, wherein the fan and the heater are disposed upstream of the second position.

8. The device of claim 1, wherein the sensor comprises a chemical analyzer selected from the group consisting of an ion-mobility spectroscope, a gas chromatograph; a gas chromatograph plus a mass spectroscope, and a flame ionization spectroscope.

9. The device of claim 1, wherein the communicator is a wireless transmitter.

10. The device of claim 1, wherein the trap comprises a filter for capturing the VOC molecules from the air, the filter including polyacrylamide fibers; and the sensor comprises an electrode for responding to a physical property change in the polyacrylamide fibers caused by the 3H3MH acid in the captured VOC molecules.

11. The device of claim 10, wherein the physical property change is at least one of electrical conductivity and electrical capacitance.

12. The device of claim 10, wherein the physical property change produces visible light emission for transmission to the communicator.

13. The device of claim 10, wherein the polyacrylamide fibers are doped with at least one of electrically-conductive metal particles and an electrically conductive polymer.

14. The device of claim 10, wherein the polyacrylamide fibers are doped with electrically-conductive metal particles.

15. The device of claim 14, wherein the electrically-conductive metal particles are nanoparticles from the group consisting of gold, silver and copper.

16. The device of claim 3, wherein the trap includes a fan for drawing the released VOC molecules to the sensor and a filter for capturing the VOC molecules from the air, the filter including polyacrylamide fibers, the sensor comprises an electrode for responding to a physical property change in the polyacrylamide fibers caused by the 3H3MH acid in the captured VOC molecules.

17. The device of claim 16, wherein the polyacrylamide fibers are doped with at least one of electrically-conductive metal particles and an electrically conductive polymer.

18. The device of claim 17, wherein the electrically-conductive metal particles are nanoparticles from the group consisting of gold, silver and copper.

19. The device of claim 16, wherein the polyacrylamide fibers are doped with polyanniline.

20. The device of claim 1, wherein the sensor also detects a threshold quantity of 3-methyl-2-hexanoic (3M2H) acid among the VOC molecules.

21. The device of claim 10, wherein the electrode responds to a physical property change in the polyacrylamide fiber caused by 3M2H acids in the captured VOC molecules.

22. The device of claim 16, wherein the electrode responds to a physical property change in the polyacrylamide fibers caused by 3M2H acids in the captured VOC molecules.

* * * * *